(12) United States Patent
Kirkpatrick et al.

(10) Patent No.: US 7,399,785 B2
(45) Date of Patent: *Jul. 15, 2008

(54) N-OXIDES AND DERIVATIVES OF MELPHALAN FOR TREATING DISEASED STATES ASSOCIATED WITH HYPOXIA INDUCIBLE FACTOR

(75) Inventors: Lynn Kirkpatrick, Tucson, AZ (US); Garth Powis, Tucson, AZ (US); Sarah J. Welsh, Oxford (GB)

(73) Assignee: Prolx Pharmaceuticals Corp., Tucson, AZ (US)

( * ) Notice: Subject to any disclaimer, the term of this patent is extended or adjusted under 35 U.S.C. 154(b) by 275 days.

This patent is subject to a terminal disclaimer.

(21) Appl. No.: 10/929,156

(22) Filed: Aug. 30, 2004

(65) Prior Publication Data

US 2005/0026872 A1 Feb. 3, 2005

Related U.S. Application Data

(63) Continuation of application No. 10/288,888, filed on Nov. 6, 2002, now abandoned.

(51) Int. Cl.
*A61K 31/19* (2006.01)
(52) U.S. Cl. .......................... 514/557; 562/452; 564/13
(58) Field of Classification Search ................. 562/452; 564/13; 514/557
See application file for complete search history.

(56) References Cited

U.S. PATENT DOCUMENTS 5,602,278 A 2/1997 Kirkpatrick

OTHER PUBLICATIONS

Kirkpatrick et al., Anti-Cancer Drugs, 1994, 5:467-472.*
Welsh et al., Molecular Cancer Therapeutics, 2004, 3(3): 233-244.*
Welsh, Sarah J., et al.; PX-478—A Potent Inhibitor of Hypoxia-Inducible Factor-1 and Anti-Tumor Agent; Nov. 19-22, 2002 AACR-EORTC-NCI Meeting, Frankfurt, Germany.
Žalgeviciene, Violeta, et al..; E*mbryotoxicity and teratogenicity of some derivatives of chloroethylaminophenylacetic acid*; Pathology Oncology Research; vol. 4, No. 1, 1998; pp. 27-29.

* cited by examiner

*Primary Examiner*—Rei-tsang Shiao
(74) *Attorney, Agent, or Firm*—Pepper Hamilton LLP

(57) ABSTRACT

This invention relates to compounds which are N-oxides and derivatives thereof, as well as their use to treat HIF related diseases. These compounds have the general formula set out below and are used to treat a variety of diseases associated with HIF:

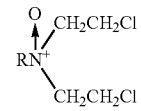

wherein R is an alkyl, aryl, arakyl or derivatives thereof such as $CH_3OCH_2CH_2-$, $CH_3CH_2OCH_2CH_2-$, $C_6H_5OCH_2CH_2-$, $C_6H_5CH_2-$, $CH_3(CH_2)_3OCH_2CH_2Cl$; or any one of the following:

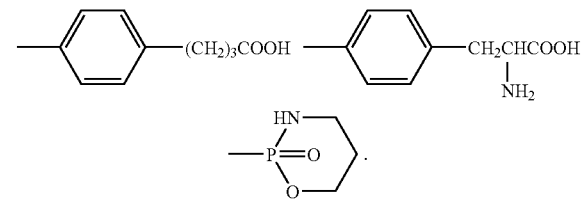

19 Claims, 18 Drawing Sheets wherein R is an alkyl, aryl or derivative thereof, or any of the following:

PX-478 malphalan

PX-478 malphalan 2HCl

A

B

A

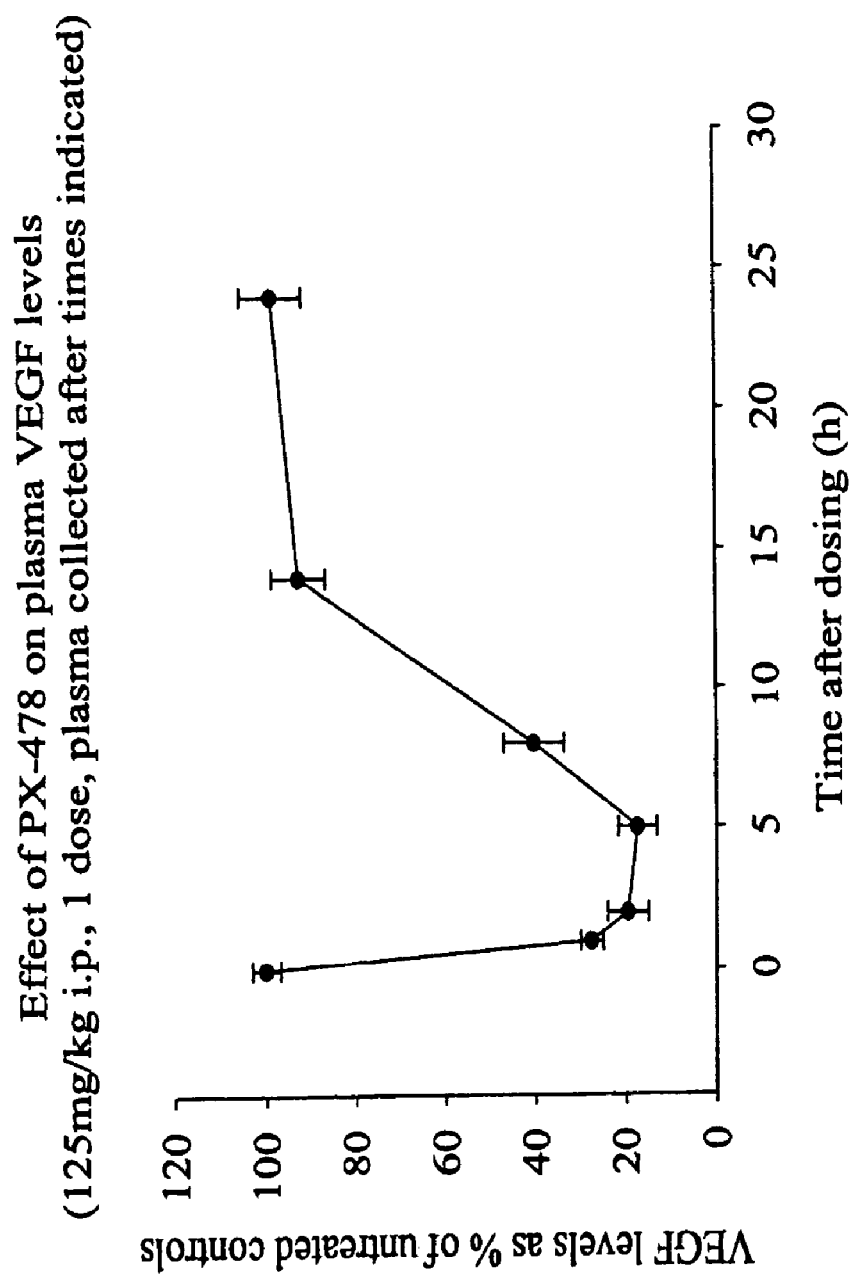

N-OXIDES AND DERIVATIVES OF MELPHALAN FOR TREATING DISEASED STATES ASSOCIATED WITH HYPOXIA INDUCIBLE FACTOR

CROSS REFERENCE TO RELATED APPLICATIONS

This case claims priority to and is a continuation of currently pending U.S. Application Ser. No. 10/288,888 filed Nov. 6, 2002, now abandoned entitled "N-OXIDES AND DERIVATIVES OF MELPHALAN FOR TREATING DISEASED STATES ASSOCIATED WITH HYPOXIA INDUCIBLE FACTOR" which is incorporated herein by reference in its entirety.

REFERENCE TO GOVERNMENT GRANT

This invention was made with government support under U19 CA052995, U54 CA090821 and RO1 CA098920 awarded by NIH. The government has ceratain rights in this invention.

FIELD OF INVENTION

The present invention relates to compounds, compositions, and formulations of N-oxides and derivatives thereof, particularly to N-oxides and derivates thereof that are useful in treating diseased states due to their effect as inhibitor of Hypoxia Inducible Factor. The present invention includes a method of treating patients in need thereof with a pharmaceutical formulation containing such compounds, compositions and formulations. A particularly useful aspect of the present invention is the ability of the compounds, compositions and formulations of the present invention to block VEGF formation to thereby affect diseases associated therewith.

BACKGROUND AND SUMMARY OF THE INVENTION

Chlorambucil derivatives have been previously described in U.S. Pat. No. 5,602,278 ("the '278 patent"), which is incorporated herein in its entirety by reference thereto. The '278 patent describes the use of chlorambucil and N-oxide derivates thereof in hypoxic environments, and more particularly chlorambuci in combination with hydralazine to create such reactive conditions. However, the complexity of tumor condition and the value of N-oxides derivatives in treating a range of diseases associated with hypoxia-inducible factor was not appreciated by the '278 patent.

A number of people have studied the N-oxide derivative of chlorambucil to determine whether this agent would provide selective toxicity to hypoxic tumor cells. Some studies have reported that the N-oxide of chlorambucil are ineffective as anti-tumor agents because this derivative is not preferentially toxic under hypoxia. Others reported that the N-oxide of chlorambucil showed no enhancement of hypoxic selectivity beyond the value for chlorambucil. However, the '278 patent demonstrated that chlorambucil and its rearranged product was effective when administered with hydralazine to thereby create a hypoxic environment.

This invention relates to pharmaceutical formulations containing compounds of the present invention. The formulation may also comprise one or more of such compounds together with one or more of a pharmaceutically acceptable carrier, a diluent, an aqueous solution, an adjuvant, or another compound useful in treating various medical conditions.

This invention also includes a method of medical treatment comprising the use of such compounds. The method may also comprise using such compounds together with other methods of medical treatment.

BRIEF DESCRIPTION OF THE FIGURES

Various aspects and applications of the present invention will become apparent to the skilled artisan upon consideration of the brief description of the figures and the detailed description of the invention, which follows:

FIG. 15 illustrates the effect of PX-478 on plasma VEGF levels (125 mg/kg i/p., 1 dose, plasma collected after times indicated).

DETAILED DESCRIPTION OF THE INVENTION

One aspect of the present invention relates to Nitrogen mustard compounds which are N-oxides and derivatives thereof. These compounds have the general formula set out below and are used for a variety of purposes:

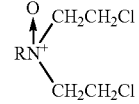

wherein R is an alkyl, aryl, aralkyl, or derivatives thereof such as CH₃OCH₂CH₂—, CH₃CH₂OCH₂CH₂—, C₆H₅OCH₂CH₂—, C₆H₅CH₂—, CH₃(CH₂)₃OCH₂CH₂Cl; or any one of the following:

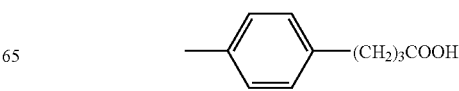

-continued

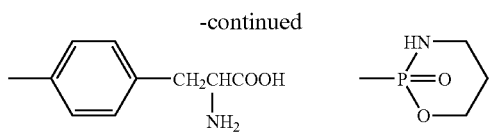

The invention also relates to salts of the above compounds. The salt would generally have the formulas set out above with a salt, wherein the salt and may be HCl, acetate, tosylate or picrate, and wherein R is as set out above.

Another aspect of the present invention, is the treatment of diseases by inhibiting HIF, particularly HIF-1α. Just a few of the diseases that may be treated with the compounds, compositions and formulation of the present invention include diseases associated with angiogensis or neovascularization. Diseases associated with HIF which may be treated include choroidal and retinal neovascularization, age-related macular degeneration, joint disease, inflammation, nuerodegenerative diseases, and ischemic injury.

Another aspect of the present invention relates to pharmaceutical formulations containing such compounds. The formulation may also comprise one or more of such compounds together with one or more of a pharmaceutically acceptable carrier, a diluent, an aqueous solution, an adjuvant, or another compound useful in treating various medical conditions.

The invention includes a method of medical treatment comprising the use of such compounds. The method may also comprise using such compounds together with other methods of medical treatment.

Figure 1:
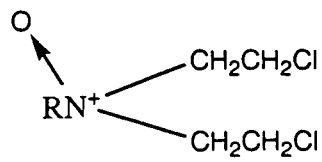
FIG. 1 illustrates compounds in accordance with the present invention.
Figure 1:
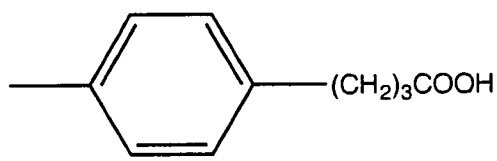
Figure 1:
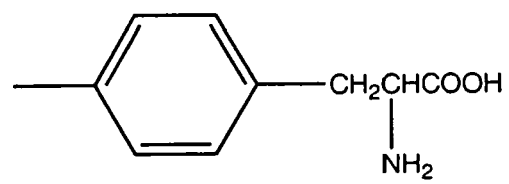
Figure 1:
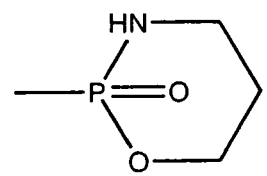
Figure 1A:
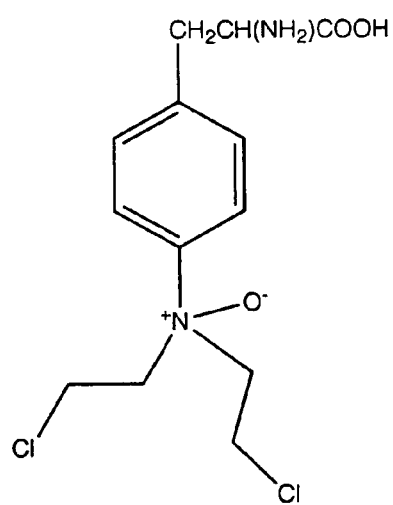
FIG. 1A illustrates the chemical structure of melphalan N-oxide and melphalan N-oxide hydrochloride.
Figure 1A:
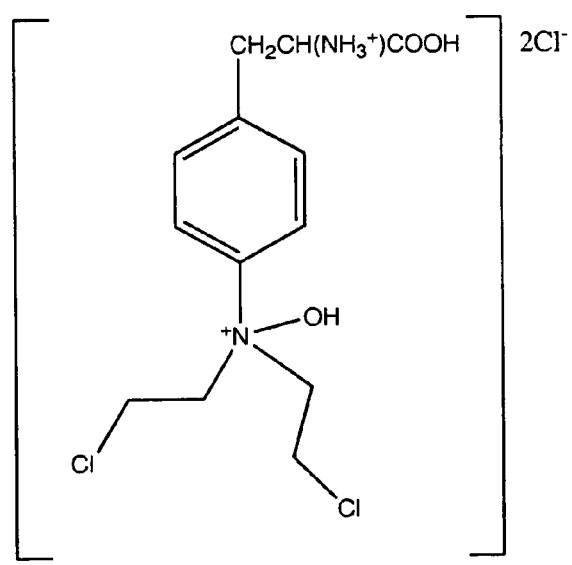

The '278 patent described in vitro and in vivo results the N-oxide derivative of chlorambucil (CHLN-O) and of the hydroxylamine derivative of chlorambucil (CHL-HD). Both compounds had a greater toxicity with reducing enzymes under hypoxia. Such biological activity was unexpected in view of the other reported results and in view of their molecular structure. Furthermore, both CHLN-O and CHL-HD were stable and produced minimal in vivo toxicity. This surprising in vitro and in vivo activity and minimal in vivo toxicity indicated that compounds of the general formula shown in FIG. 1 would be useful in pharmaceutical formulations for treating hypoxic tumor cells. However, relatively small portions of a tumor may be under hypoxic conditions at any given time. Also, the only in vivo data reported related to the chlorambucil derivative 4[p-(N-2-chloroethoxy N-2 chloro ethylamino)phenyl]butanoic acid. Additionally, there was little appreciation of the effect of the chlorambucil derivatives discussed therein on HIF, angiogenesis, glycolysis, enthropoiesis, apoptosis, VEGF, or HIF.

Solid tumors with areas of hypoxia have long been recognized as the most aggressive and difficult tumors to treat. The cellular response to hypoxia includes increased glycolysis, inhibited apoptosis, and increased angiogenesis and metastasis, and is mediated through the hypoxia-inducible factor-1 (HIF-1) transcription factor, a heterodimer of HIF-1α and HIF-1β subunits. Since the levels of HIF-1α have been shown to control the activity of HIF-1 and are over expressed in a range of human tumors, HIF-1α is an attractive target for chemotherapy.

PX-478 (S-2-amino-3-[4'-N,N,-bis(2-chloroethyl)amino] phenyl propionic acid N-oxide dihydrochloride) or melphalan N-oxide and derivatives thereof significantly decreases the hypoxia-induced increase in HIF-1α protein but does not affect HIF-1β, inhibits HIF-1 transactivation and decreases the expression of the downstream target gene vascular endothelial growth factor (VEGF), in both human breast carcinoma MCF-7 cells and human colon carcinoma HT-29 cells. Human renal cell carcinoma (RCC4 cells) lacking active von Hippel Lindeau protein (pVHL) that regulates the breakdown of HIF-1α and RCC4/VHL cells into which active pVHL has been reintroduced were used to show that PX-478 acts independently of the pVHL pathway. Therefore, PX-478 is one of the first specific inhibitors of the HIF-1 pathway and a promising new class of HIF inhibiting agents.

HIF-1 is a heterodimer of the oxygen regulated HIF-1α or HIF-2α and constitutively expressed HIF-1β and it activates transcription of a wide variety of genes involved in glycolysis, erythropoiesis, resistance to apoptosis, and promotion of angiogenesis.

The activity of HIF-1 appears to be primarily controlled by levels of HIF-1α and HIF-2α subunits. Under normoxic conditions levels of HIF-1α and HIF-2α are kept very low as specific proline residues in the oxygen-degradation domain (ODD) ($Pro^{564}$ and $Pro^{402}$ in human HIF-1α) are hydroxylated by a family of prolyl 4-hydroxylases. This allows the von Hippel Lindau (pVHL) protein to bind to the ODD of HIF-1α leading to the recruitmen of a complex that activates E3 ubiquitin ligase resulting in ubiquitination of HIF-1α, ultimately, its proteosomal degradation. Prolyl 4-hydroxylases show an absolute requirement for $O_2$, $Fe^{2+}$ and 2-oxoglutarate or ascorbate. Therefore, under hypoxia (<5% oxygen) the prolyl hydroxylases are inhibited and levels of HIF-1α protein increase, binding with the constitutively expressed HIF-1β subunits to give a complex then binds to hypoxic response element (HRE) DNA sequences in the promoters region of HIF-1 responsive genes to activate their transcription.

Other pathways also regulate HIF-1α degradation including the tumor suppressor p53 which binds to HIF-1α resulting in degradation of both proteins by recruitment of MDM2, another E3 ubiquitin-ligase. The heat shock protein-90 (HSP90) protein, a molecular chaperone, may be involved in HIF-1α degradation since the HSP90 inhibitor geldanamycin inhibits the hypoxia-induced increase in HIF-1α protein.

Growth factors and cytokines including insulin, insulin-like growth factors 1 and 2, epidermal growth factor, fibroblast growth factor 2, interleukin 1β, tumor necrosis factor α, transforming growth factor β1 and platelet-derived growth factor, amongst others, can stabilize and increase the levels of HIF-1α under normoxic conditions. These factors may be stabilizing HIF-1α via common cellular kinase pathways such as the mitogen activated kinase (MAPK) and phosphatidyloinositol 3-kinase (PI3K)/Akt pathways although the exact mechanism remains uncertain [X]. In addition, protein stabilization alone is not sufficient to activate HIF-1 under normoxic conditions. Full activation requires post-translational protein phosphorylation (via the PI3K/AKT pathway), nuclear transport mediated by HSP90, dimerization with HIF-1β, DNA binding and recruitment of transcriptional co-factors such as Creb binding protein (CBP)/p300 (mediated by asparaginyl hydroxylation on Asn803 in human HEF-1α), SRC-1 and TIF2 [ref]. FIH (factor inhibiting HIF-1) which is a transcriptional repressor that interacts with HIF-1α and pVHL has also recently been described. Many studies have suggested that redox-dependent processes are involved in both stabilization and activation of the HIF-1 complex. We have recently reported that the small redox protein thioredoxin-1 increases HIF-1α protein leading to increased production of vascular endothelial growth factor (VEGF) and to increased angiogenesis. A redox inactive mutant thioredoxin-1 decreased HIF-1α protein, VEGF and angiogenesis. It has also been shown that factor-1 enhances recruitment of SRC-1, TIF2 and CBP/p300 and a model has been proposed in which reduced thioredoxin translocates to the nucleus of hypoxic cells and transmits the redox signal.

HIF-1α protein is found in a wide variety of human primary tumors but only at very low levels in normal tissue. The importance of HIF-1α to cancer is demonstrated by the high incidence of tumors such as renal cell carcinoma, pheochromocytoma and hemingioblastoma of the central nervous system in individuals with loss of function of both alleles of the VHL gene leading to elevated HIF-1α levels. In addition, most cases of sporadic renal cell carcinoma are associated with an early loss of function of the VHL gene and increased HIF-1α levels. Reintroduction of the intact VHL gene into cells derived from renal carcinomas restores HIF-1α to normoxic levels and decreases tumorigenicity. HIF-1α levels are also increased in cancer cells with mutant or deleted PTEN HIF-2α which is expressed in some tumors is also found in bone marrow and tumor associated macrophages.

Because of the role of HIF-1α in regulating the response of growing tumors to hypoxia it is a very important target for anticancer drug development. U.S. Pat. No. 5,602,278 describes PX-478 (S-2-amino-3-[4'-N,N,-bis(2-chloroethyl) amino]phenyl propionic acid N-oxide dihydrochloride) as a potential agent that would be selectively activated in hypoxic environments. However, although 4[p-(N-2-chloroethoxy N-2 chloro ethylamino)phenyl]butanoic acid was shown to preferentially kill hypoxic cells, its mechanism of action remained unclear. We investigated the effects of PX-478 on HIM-1α and its downstream targets. We have shown that PX-478 treatment leads to a decrease in HIF-1α protein (both in vitro and in vivo) and subsequent transactivation of the HIF-1 complex leading to decreased levels of downstream targets, possibly through inhibition of thioredoxin-reductase. Studies also showed that the activity of PX-478 is independent of the VHL pathway. PX-478 therefore represents one of the first inhibitors of the HIF pathway and is a promising new anticancer agent.

Methods

Cell culture and hypoxia treatment. MCF-7 human breast cancer and HT-29 colon cancer cells were obtained from the American Tissue Type Collection (Manassas, Va.). Human renal cell carcinoma RCC4 cells and RCC4/VHL into which the wild-type von Hippel-Lindau (VHL) gene has been transfected were obtained from Dr. Peter Ratcliffe (Welcome Trust Centre for Human Genetics, Oxford, UK). Cells were grown under humidified 95% air, 5% $CO_2$ incubator at 37° C. in Dulbecco's modified Eagle's medium (DMEM) supplemented with 10% fetal bovine serum (FBS), and 1 mg/ml G418 where appropriate (RCC4 and RCC4/VHL cells). For exposure to hypoxia the culture flasks were incubated for various times in a humidified chamber at 37° C. with a gas mixture containing 5% $CO_2$/74% $N_2$/21% argon. Oxygen levels were kept at 1% in the gas phase using an oxygen sensor (Pro:Ox 110, Biospherix, Redfield, N.Y.). At the end of the study cells were washed twice with ice cold phosphate buffered saline, pH 7.5 (PBS). One ml of media from each flask was removed after treatment and stored at −80° C. for measurement of VEGF levels.

Cell growth and viability assays. Growth inhibition assays were carried out as described previously using the 3-[4,5-dimethylthiazol-2-yl]-2,5-diphenyltetrazolium bromide (MTT) assay. For analysis under hypoxic conditions, plates were incubated for 16 h in 1% oxygen in the presence of the drug then placed in 20% oxygen for the remainder of the 72 h.

VEGF ELISA. Approximately $10^7$ cells were lysed at 4° C. for 1 hr in 200 μl of lysis buffer (150 mM NaCl, 50 mM Tris buffer, pH 7.5, 1 mM phenylmethylsulfonyl fluoride, 2 μg/ml aprotinin, 2 μg/ml leupeptin, 0.1 mM sodium orthovanadate, 1% NP 40 and 0.2% sodium dodecyl sulfate [SDS]). The lysate was centrifuged (15 min, 4° C., 10,000×g) and the supernatant was collected. A 20 μl aliquot was removed for analysis of protein concentration (Biorad Protein Detection System, Biorad, Hercules, Calif.) and the lysate was stored at −80° C. until required. VEGF in cell lysates was expressed as pg VEGF protein/mg of total cell protein and VEGF in the medium corrected to pg VEGF protein/mg of total cell protein measured in cells from the same flask. The amount of human VEGF in cell lysates and VEGF secreted into the medium was determined using an ELISA kit that measures $VEGF_{165}$ and $VEGF_{121}$ isoforms (Human VEGF-ELISA; R&D Systems, Minneapolis, Minn.) according to the manufacturer's instructions. The amount of mouse VEGF in plasma was determined using an ELISA kit that measures mouse $VEGF_{165}$ and $VEGF_{121}$ isoforms (Mouse VEGF-ELISA; R&D Systems, Minneapolis, Minn.) according to the manufacturer's instructions.

Immunoblotting. Nuclear and cytoplasmic extracts were prepared using NE-PER™ Nuclear and Cytoplasmic Extraction Reagents (Pierce, Rockford, Ill.) according to the manufacturer's instructions. Western blotting was performed as described previously [Welsh et al] using mouse anti-human HIF-1α (1 μg/ml; Transduction Labs, Lexington, Ky.); mouse anti-human HIF-1β (1 μg/ml; SantaCruz Biotechnology, Santa Cruz, Calif.); mouse anti-human iNOS (5 μg/ml; Transduction Labs); and goat anti-human lamin A (0.5 μg/ml; SantaCruz Biotechnology). Anti-mouse or anti-goat horseradish peroxidase-conjugated secondary antibodies (Amersham Pharmacia, Uppsala, Sweden) were used at a dilution of 1:5000 for detection by chemiluminescence and blots were quantified using ImageQuant software (Molecular Dynamics, Sunnyvale, Calif.)

HIF-1α mRNA Measurement. Fifteen μg total RNA prepared using the Trizol extraction method (Life Technologies, Carlsbad, Calif.), was separated by electrophoresis in a 1.5% agarose-formaldehyde gel and transferred to a nylon membrane (Osmonics Inc., Westborough, Mass.). RNA was cross-linked to the membrane using a Stratalinker UV crosslinker (Stratagene, La Jolla, Calif.). A full-length probe to human HIF-1α, labeled with $[\alpha-^{32}P]$ dCTP using a Random Primers DNA Labeling System (Life Technologies), was hybridized to the membrane using ULTRAhyb hybridization buffer (Ambion, Austin, Tex.) and all wash steps were performed according to manufacturer protocols. Blots were imaged using the MD Storm 860 phosphorimager and were quantified using ImageQuant software (Molecular Dynamics, Sunnyvale, Calif.). A full length cDNA probe for 18S rRNA was used as a loading control.

Hypoxia Response Element Reporter Assay. The pGL3 firefly luciferase reporter plasmid containing the hypoxia response element (HRE) from phosphoglycerate kinase (PGK) [Nature paper] was supplied by Dr Ian Stratford (University of Oxford, UK). Plasmid DNA was prepared using a commercial kit (Qiagen, Valencia, Calif.). The empty pGL3 control plasmid and the pRL-CMV *renilla* luciferase containing plasmid used to control for transfection efficiency were obtained from Promega (Madison, Wis.). Cells were transfected with 5 μg of HEF-1 reporter plasmid or pGL3 control plasmid, and 0.025 μg pRL-CMV *renilla* luciferase plasmid (to control for transfection efficiency) using LipoTAXI mammalian transfection reagent (Stratagene, TX) according to the manufacturer's instructions. Twenty four hours later cells were exposed to hypoxia as previously described. Firefly and renilla luciferase activity was measured using the Dual-Luciferase Reporter Assay System (Promega, Madison, Wis.) according to the manufacturer's instructions.

Immunohistochemistry. MCF-7 and MiaPaCa cells ($10^7$ in 0.2 ml matrigel) were injected into the flanks of scid mice. When the tumors reached 0.5 g the mice (4 per group) were treated (by intraperitoneal injection) with 100 mg/kg PX-478 in XXXX or vehicle control. Four hours later, 1 ml blood was taken from each mouse, the mice were sacrificed, tumors were removed, fixed in 4% formaldehyde in PBS and embedded in paraffin. Sections were stained with antibodies to HIF-1α (10 μg/ml; Transduction Labs) or VEGF (7 μg/ml; Santa Cruz Biotechnology) using an automated immunostainer system (GenII, Ventana Medical Systems, Tucson, Ariz.). The intensity of HIF-1α staining was measured using a SimplePCI program (Compix, XX Township, XX).

Thioredoxin reductase assay. Total cell lysates were prepared as described for the VEGF ELISA. Thioredoxin reductase activity was measured as described in (Berggen et al., 1999). Briefly, 0.2 ml aliquots of fresh adenosine 2',5'-diphosphate coupled-agarose beads (ADP agarose) (Sigma) were mixed with 0.2 ml aliquots of supernatant for 1 h at 4° C. to remove endogenous thioredoxin and other small molecular weight reductants. The beads were then washed by recentrifugation at 1000×g with 2×1 ml of 0.1M NaCl and thioredoxin reductase was eluted with 0.5 ml of 1.0M KCL. Thioredoxin reductase activity was then measured as the oxidation of NADPH at 339 nm, using 5 μM human recombinant thioredoxin as substrate and oxidized insulin as the final electron acceptor. Activity was expressed as nanomoles NADPH oxidized per minute per milligram of supernatant protein.

Immunohistochemistry. Human breast carcinoma MCF-7 cells ($10^7$ cells in matrigel per mouse) were injected subcutaneously into the flanks of scid mice implanted with estrogen pellets. Tumors were allowed to grow to 0.5 g. The mice then received intraperitoneal vehicle alone or 120 mg/kg PX-478. Four hours later the tumors were excised, fixed in formalin and embedded in paraffin. Sections were stained with antibodies to HRF-1α (10 μg/ml; Transduction Labs) or VEGF (7 μg/ml; Santa Cruz Biotechnology) using an automated immunostainer system (GenII, Ventana Medical Systems, Tucson, Ariz.). Staining was quantified using Simple PCI analysis software (Compix).

Discussion

PX-478 shows inhibition in hypoxia and normoxia. Human breast carcinoma and human colon carcinoma HT-29 cells were treated for 16 h with varying concentrations of PX-478 in the presence of normoxia (20% oxygen) or hypoxia (1% oxygen). The cells were then washed three times with warm drug-free medium and incubated for the remainder of 72 h. The MTT assay was then carried out to determine growth inhibition. Data represent the mean±SE from three experiments carried out in duplicate. PX-478 shows growth inhibition under hypoxia (1% oxygen) and normoxia (20% oxygen) (p=<0.01) with a ratio of growth inhibition under hypoxia to that in normoxia at 1.25 in MCF-7 cells and 1.20 in HT-29 cells. Table 1 below illustrates these results:

TABLE 1

| Cell line | $IC_{50}$ (μM) | |
| --- | --- | --- |
| | Normoxia | Hypoxia |
| MCF-7 | 25.1 ± 1.5 | 20.0 ± 2.0 |
| HT-29 | 29.5 ± 2.4 | 23.9 ± 2.3 |

Figure 2:
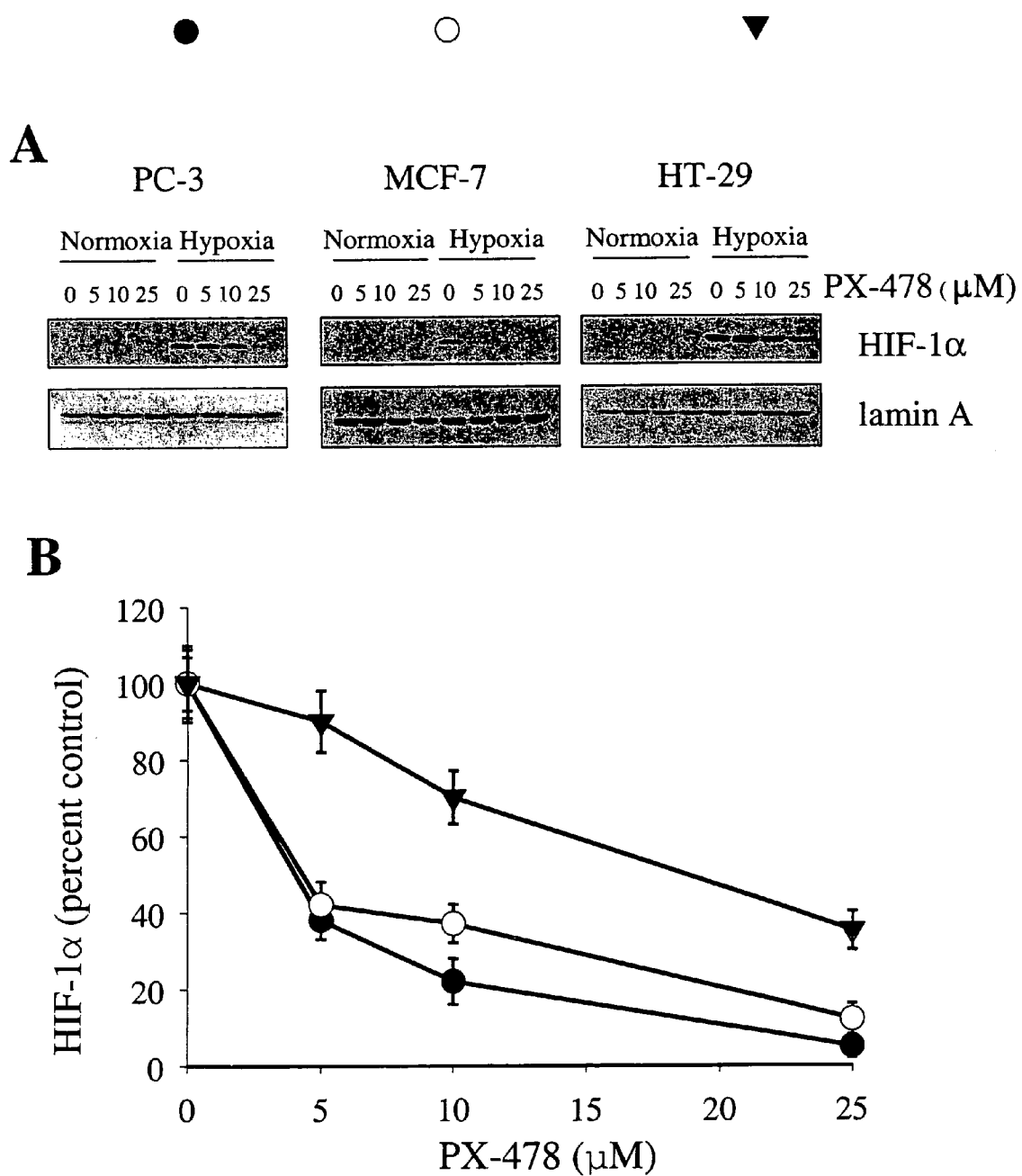
FIG. 2 illustrates the effect of PX-478 on HIF-1α protein levels.

PX-478 inhibits HIF-1α protein. HIF-1α is a key controller of the cellular response to hypoxia. Therefore we examined the effect of PX-478 on HIF-1α protein levels. A, PC-3 prostate cancer, MCF-7 breast cancer and HT-29 colon cancer cells were exposed to 16 h in hypoxia (1% oxygen) in the presence of PX-478. Nuclear cell extracts were prepared and levels of HIF-1α protein was measured using Western blotting. The results show a typical Western blots with lamin A as a loading control. B, Data are the mean±S.E. of 3 experiments. (●) PC-3 prostate cancer, (○) MCF-7 breast cancer and (▼) HT-29 human colon cancer. PX-478 inhibits hypoxia-induced (1% oxygen) HIF-1α protein in human breast carcinoma MCF-7 (FIG. 2A) and human colon carcinoma HT-29 (FIG. 2B) cells with $IC_{50}$ values of 3.5±2.0 and 17.8±5 μM respectively. HIF-1α protein levels were very low under normoxia (20% oxygen) as reported previously (Welsh et al., 2002) so no effect was seen. However, an $IC_{50}$ value of 2.5±1.2 μM was obtained in human pancreatic carcinoma PC-3 cells which show detectable levels of HIF-1α protein in normoxia (data not shown). A similar $IC_{50}$ value was obtained in hypoxic conditions for this cell line (2.1±2.0 μM). MCF-7 human breast cancer (A) and HT-29 human colon carcinoma cells (B) were treated for 16 h in normoxia (20% oxygen) or hypoxia (1% oxygen) in the presence of PX-478. Nuclear cell extracts were prepared and levels of HIF-1α and HIF-1β proteins were measured using Western blotting. Blots are representative of 3 experiments. Lamin A was used as a loading control.

Figure 3:
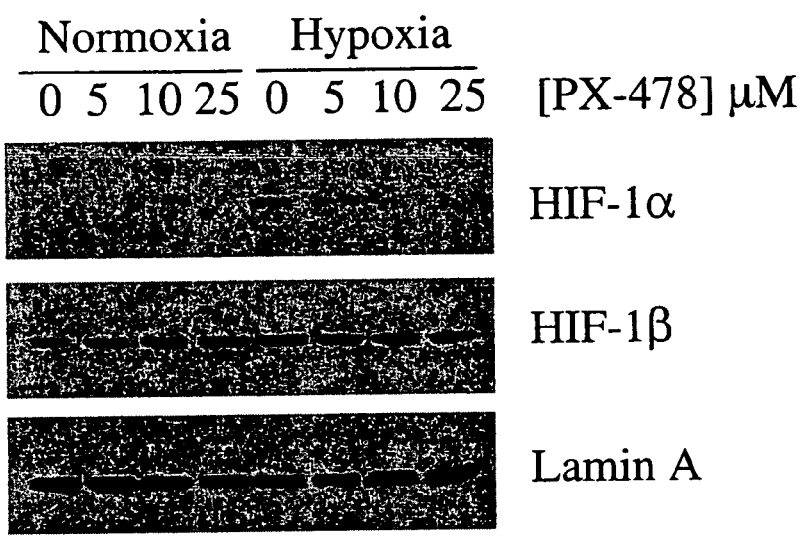
FIG. 3 illustrates the effect of PX-478 on HIF-1α and HIF-1β protein levels.
Figure 3:
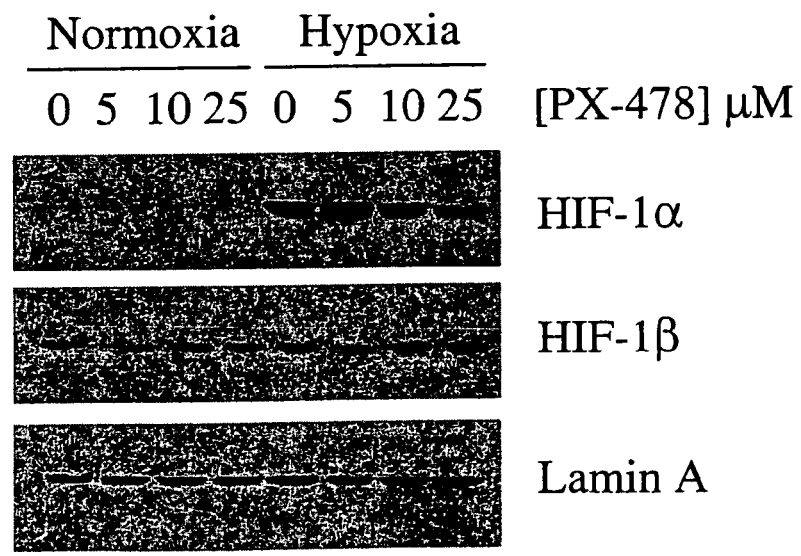

No effect of PX-478 was seen on HIF-1β levels (FIGS. 3A and 3B) or HIF-1α mRNA levels (data not shown) in any of the cell lines.

Figure 4:
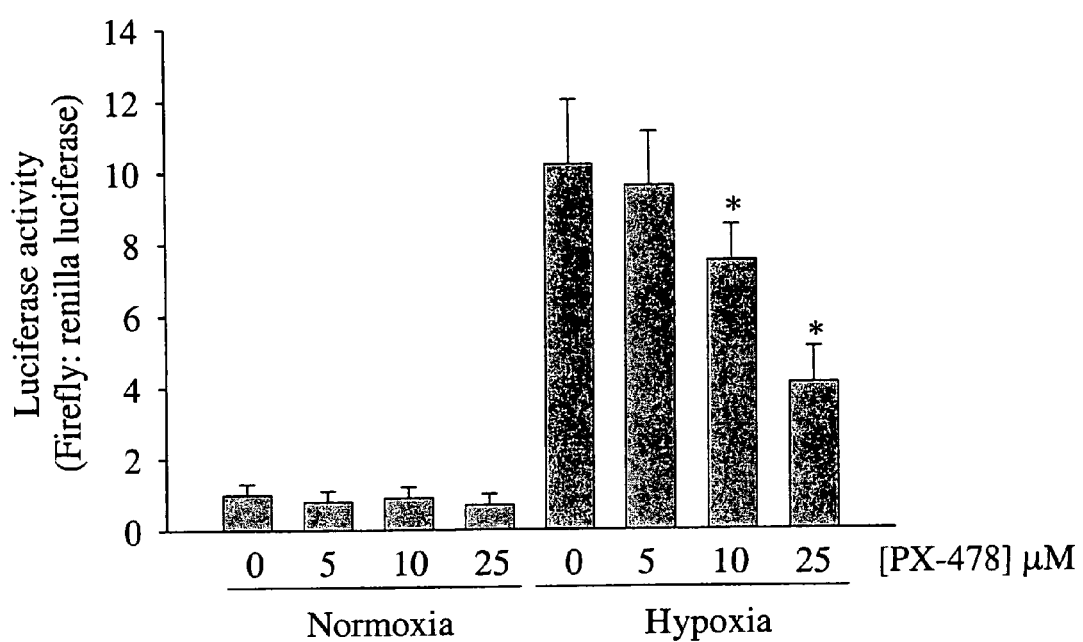
FIG. 4 illustrates the effect of PX-478 on HIF-1 transactivation.
Figure 4B:
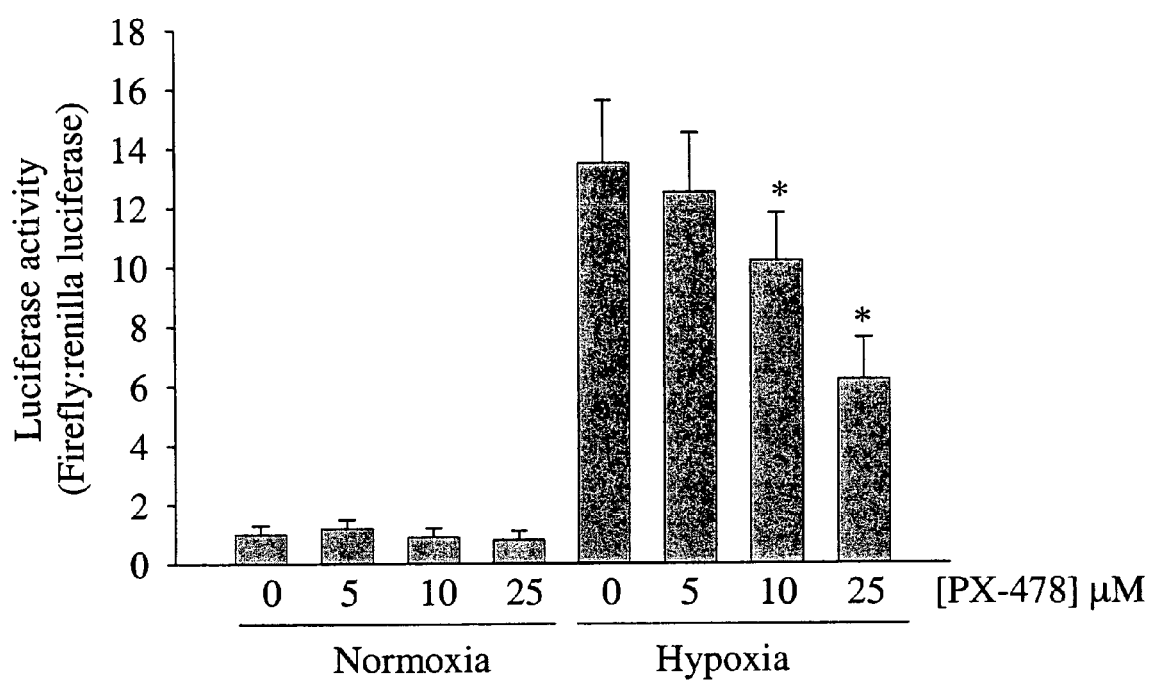

PX-478 inhibits hypoxia-induced HIF-1 transactivation. HIF-1 transactivation was measured by transiently transfecting cells with a construct expressing luciferase under the control of multiple copies of the HRE from PGK. MCF-7 human breast carcinoma (A) or HT-29 human colon carcinoma (B) cells were treated for 16 h in normoxia (20% oxygen) or hypoxia (1% oxygen) in the presence of varying concentrations of PX-478. HIF-1 transactivation was then measured using a construct expressing firefly luciferase under the control of several copies of the HRE from PGK. Renilla luciferase was co-transfected as a control for transfection efficiency. Data represent the mean±SE from 3 experiments. *shows a significant change from untreated controls under the same conditions (p=<0.001). HT-29 cells (FIG. 4B) showed significantly greater transactivation of HIF-1 compared to MCF-7 cells (FIG. 4A) (13.9±1.5 compared to 10.1±1.9 fold respectively) (p=<0.01). However, PX-478 significantly decreased hypoxia-induced transactivation of HIF-1 in both cell lines after 16 h treatment with 10 and 25 μM PX-478 (p=<0.01). $IC_{50}$ values for inhibition of the hypoxia-induced transactivation were 20.5±1.4 and 23.1±1.8 μM for MCF-7 and HT-29 cells respectively. HIF-1 transactivation was very low under normoxia and was not affected by treatment with PX-478 in either cell line.

Figure 5:
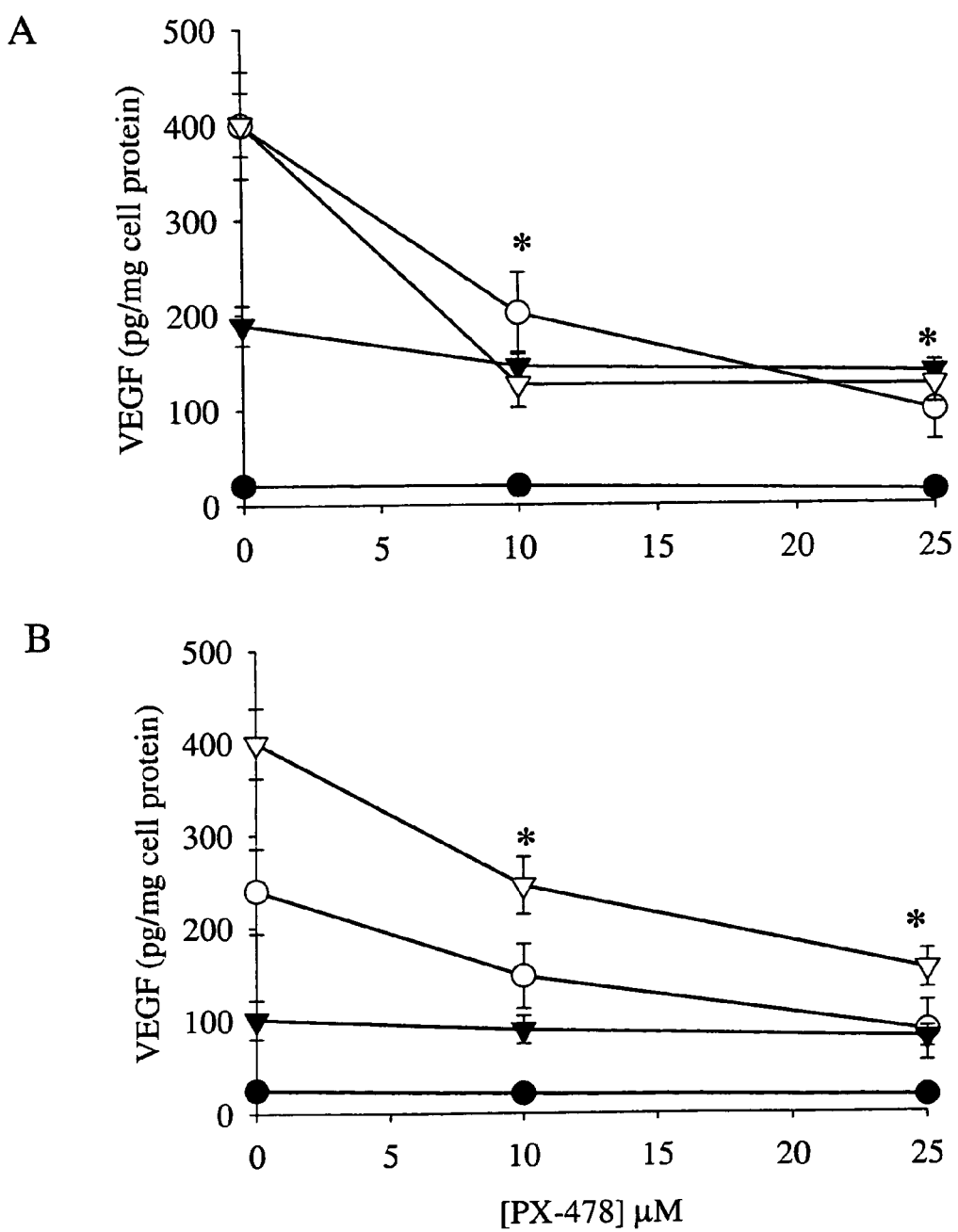
FIG. 5 illustrates the effect of PX-478 on VEGF.
Figure 6:
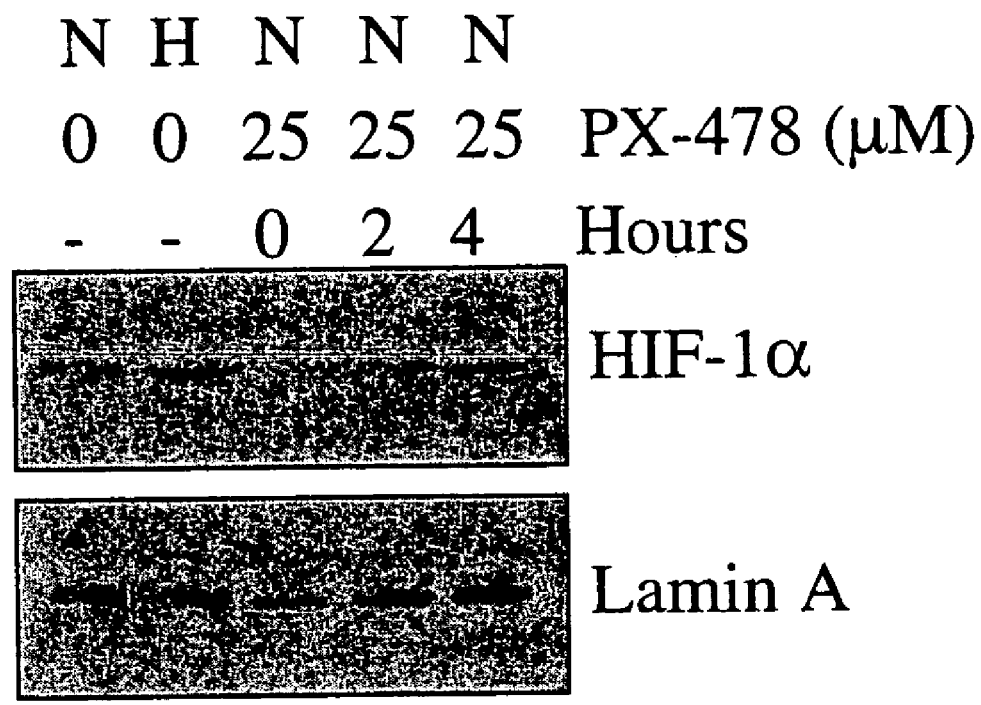
FIG. 6 illustrates the recovery of HIF-1α protein after inhibition.

PX-478 inhibits hypoxia-induced VEGF production. MCF-7 human breast carcinoma (A) and HT-29 human colon carcinoma (B) cells were treated for 16 h in normoxia (20% oxygen; filled symbols) or hypoxia (1% oxygen; open symbols) in the presence of PX-478. VEGF levels in cell lysates (circles) or the medium (triangles) were then measured using ELISA. Data represent the mean±SE from 3 experiments. * shows a significant difference from untreated controls under the same condition (normoxia or hypoxia) (p=<0.001). PX-478 significantly decreased levels of hypoxia-induced VEGF protein after treatment for 16 h with 10 µM PX-478 (p=<0.01) in both MCF-7 and HT-29 cells (FIGS. 5A and B respectively). $IC_{50}$ values were 17.1±4.0 and 13.5±4.0 µM for VEGF in cell lysates and 3.8±2.0 and 11.5±2.5 µM for VEGF secreted into the medium, in MCF-7 and HT-29 cells respectively. Levels of VEGF secreted into the medium were decreased to normoxic levels after treatment with 10 µM PX-478 in MCF-7 cells. However neither the levels of VEGF in cell lysates in MCF-7 cells or those in cell lysates or secreted into the medium in HT-29 cells returned to normoxic levels after treatment with 25 µM PX-478. Interestingly, PX-478 did not affect VEGF levels in normoxia in either cell line.

HIF-1α protein remains inhibited for up to 4 h after removal of PX-478. To investigate how long HIF-1α protein remains inhibited after treatment of cells with PX-478, MCF-7 cells were treated for 16 h with PX-478, the drug was then washed out and recovery of HIF-1α was measured MCF-7 human breast carcinoma cells were exposed to hypoxia (1% oxygen, H) for 16 h and were then treated with 25 µM PX-478 for up to 4 h. Nuclear cell extracts were prepared at the time points indicated and Western blotting was performed to measure levels of HIF-1α protein. Levels of HIF-1α protein after 16 h under normoxia (20% oxygen; N) are also shown as a control. HIF-1α protein levels returned to pre-treatment levels within 4 h of removal of the drug.

Figure 7:
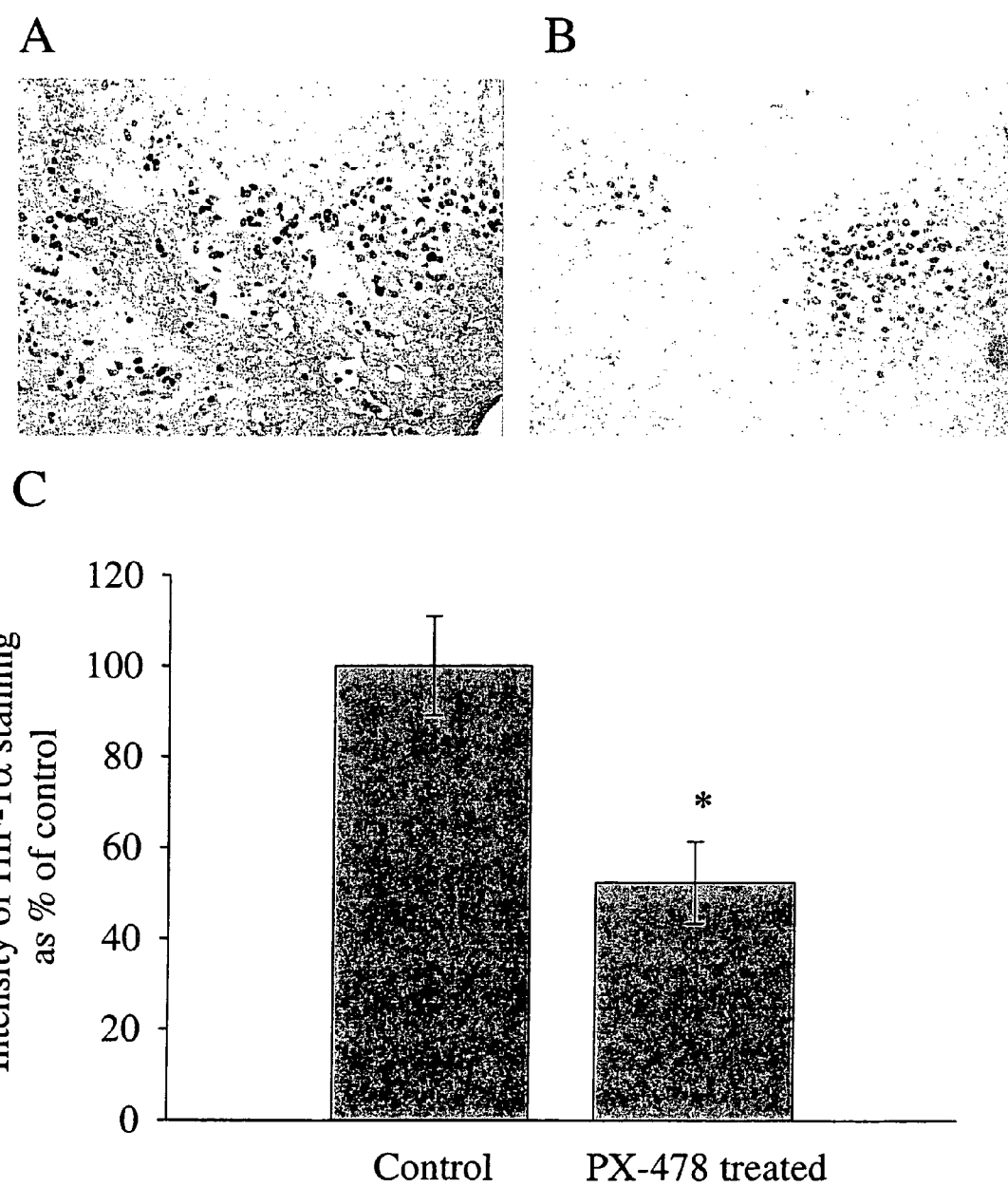
FIG. 7 illustrates the effect of PX-478 in vivo.

PX-478 inhibits HIF-1α protein in vivo. MCF-7 cells were grown as xenografts in the flanks of scid mice. When the xenografts reached 0.3 g the mice were treated with (A) vehicle control or (B) 100 mg/kg PX-478 (4 per group). Four hours later tumors were then removed, formalin fixed, embedded in paraffin and the level of HIF-1α protein was measured using immunohistochemistry (A and B). (C) The intensity of HIF-1α staining was quantified using Simple PCI software. * shows a significant difference from controls (p=<0.01). Data represent the mean±SE. Treatment of MCF-7 cells grown as xenografts in the flanks of scid mice showed significantly decreased levels of HIF-1α protein after 4 h treatment with PX-478 (p=<0.005) (FIGS. 7A and 7B). Staining remained nuclear in localisation even in PX-478 treated cells but levels of HIF-1α were decreased to 50% in PX-478 treated mice compared to untreated controls (FIG. 7C).

Figure 8:
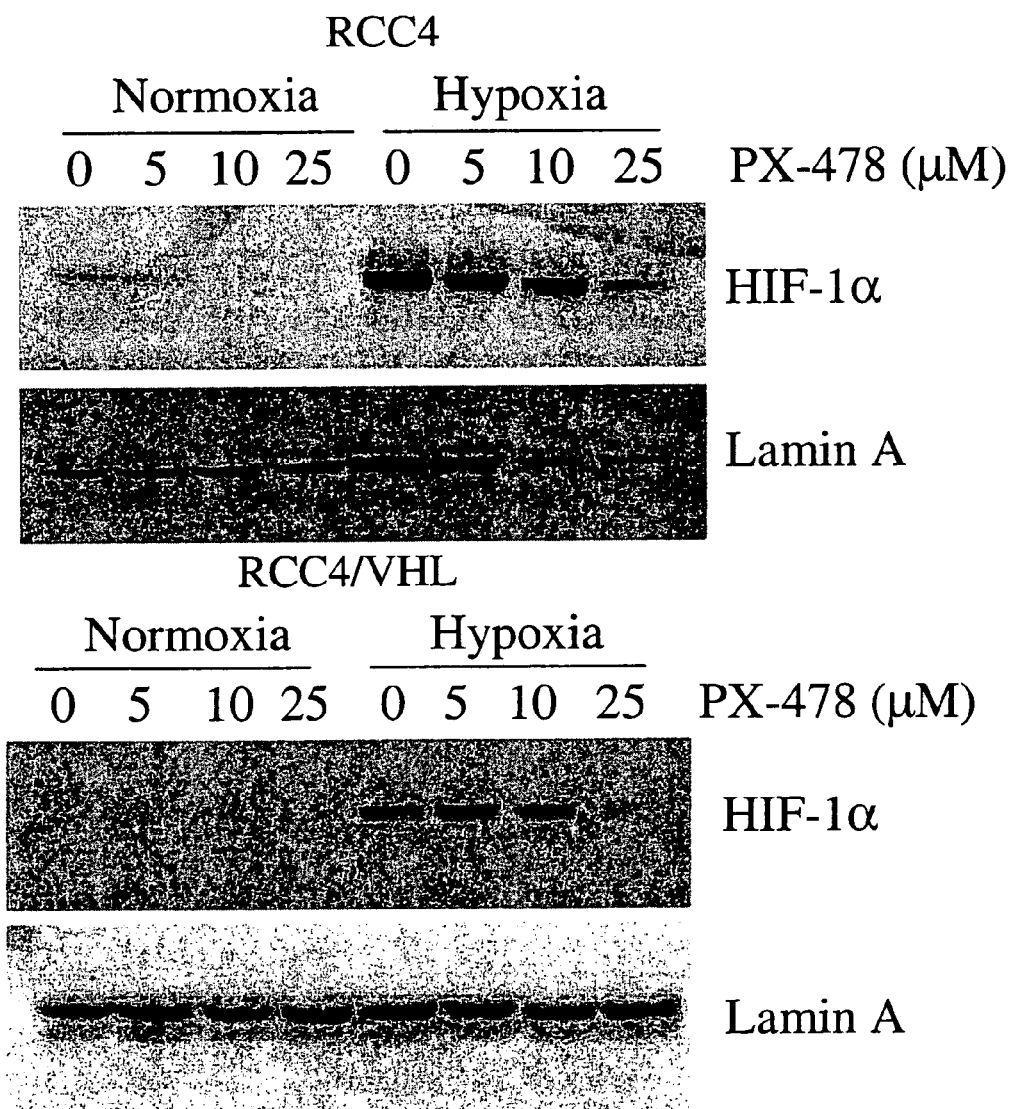
FIG. 8 illustrates the effect of VHL on effect of PX-478.

PX-478 inhibits HIF-1α via a VHL-independent pathway. Human renal carcinoma RCC4 and RCC4/VHL cells were treated for 16 h with varying concentrations of PX-478 in the presence of normoxia (20% oxygen) or hypoxia (1% oxygen). (A) HIF-1α protein levels were then measured in nuclear extracts. Lamin A was used as a loading control. (B) HIF-1 transactivation was also measured using a construct expressing luciferase under the control of multiple copies of the HRE from PGK. Renilla luciferase was co-transfected to correct for transfection efficiency. Data represent the mean±SE. * shows a significant difference from the untreated sample under the same condition (p=<0.01). Human renal carcinoma cells lacking the VHL gene (RCC4) and RCC4/VHL cells into which the VHL gene has been replaced were used to investigate the mechanism of inhibition of HIF-1α by PX-478. RCC4 cells express high levels of HIF-1α protein even under normoxia, whereas RCC4/VHL cells express low levels of HIF-1α under normoxia (FIG. 8A). PX-478 inhibited HIF-1α protein in RCC4 cells under both normoxic ($IC_{50}$=5.1±2.0 µM) and hypoxic conditions ($IC_{50}$=16.9±1.9 µM) indicating that PX-478 decreases HIF-1α independently of the VHL pathway (FIG. 8A). PX-478 also inhibited hypoxia-induced HIF-1α in RCC4/VHL cells with an $IC_{50}$ of 18.1±4.0 µM (FIG. 8A).

Figure 8B:
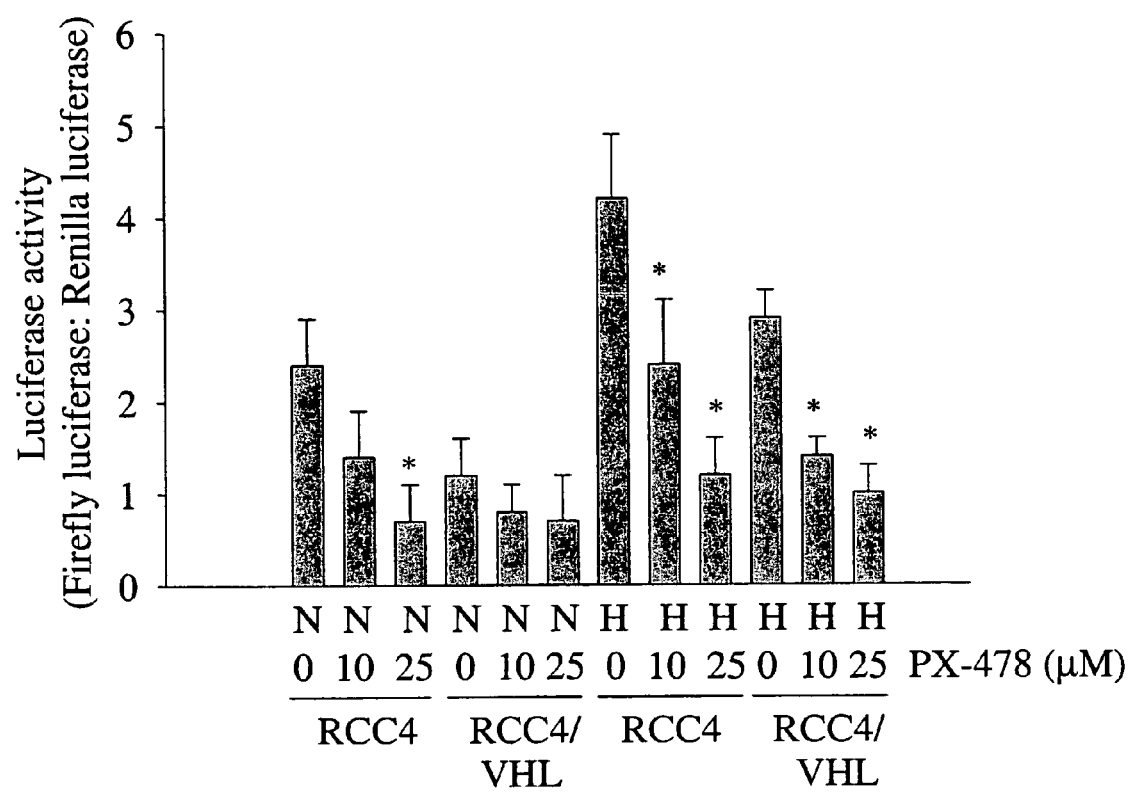
Figure 9:
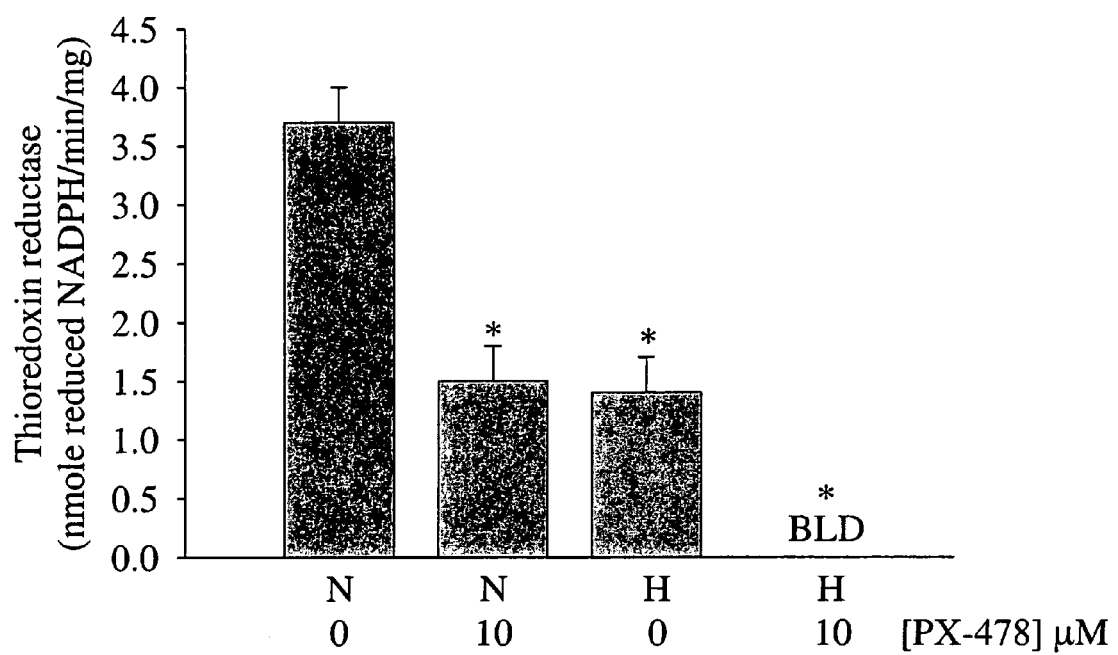
FIG. 9 illustrates the effect of PX-478 on thioredoxin reductase.

Transactivation of HIF-1 was also significantly inhibited in RCC4 cells under both normoxia and hypoxia (FIG. 8B) with $IC_{50}$ values of 12.5±2.5 µM and 10.1±1.2 µM respectively, confirming that PX-478 acts independently of the VHL pathway. RCC4/VHL cells showed similar responses to PX-478 as MCF-7 and HT-29 cells as although an $IC_{50}$ of 13.5±1.3 µM was obtained for inhibition of hypoxia-induced HIF-1 transactivation, PX-478 did not affect transactivation in normoxia, although levels were very low (FIG. 8B).

PX-478 inhibits thioredoxin reductase. Our previous studies have shown that inhibition of redox signaling through thioredoxin can decrease HIF-1α protein levels, decrease HIF-1 transactivation leading to decreased levels of the HWF-1 downstream targets VEGF and iNOS. Therefore we investigated the effect of PX-478 on thioredoxin reductase activity HT-29 cells were exposed to normoxia (20% oxygen; N) or hypoxia (1% oxygen; H) for 16 h in the presence of 0 or 10 µM PX-478. Cells were lysed and thioredoxin reductase activity was measured. * shows a significant difference from the untreated control in normoxia. BLD denotes below the limit of detection of the assay. Data represent the mean±SE of at least 2 experiments carried out in duplicate. Treatment of MCF-7 cells with 10 µM PX-478 significantly decreased thioredoxin reductase activity by 40% in normoxia (p=<0.001). Hypoxia itself also significantly decreased thioredoxin reductase activity to a similar extent, however thioredoxin reductase activity was decreased to below the limit of detection of the assay after treatment with 10 µM PX-478 under hypoxic conditions.

Hypoxia inducible factor-1 (HIF-1) plays a central role in the development and progression of tumors. While not wishing to be bound by theory it appears this is because HIF-1 controls the expression of a more than 40 target genes whose protein products play crucial roles in allowing the survival of cells under adverse environmental conditions and in response to radiation or chemotherapy. These include the gene encoding VEGF, which is required for tumor angiogenesis, insulin-like growth factor 2 (IGF2), which promotes tumor cell survival, and glucose transporters 1 and 3, and glycolytic enzymes such as aldolase A and C, hexokinase 1 and 3, lactate dehydrogenase A and PGK. Many human tumors have been shown to over-express HIF-1α protein as a result of intratumoral hypoxia and genetic alterations affecting key oncogenes and tumor suppressor genes. In addition over-expression of HIF-1α correlates with treatment failure and mortality. However, loss of HIF-1 activity has dramatic negative effects on tumor growth, vascularization and energy metabolism in xenograft assays. Therefore inhibition of HIF-1 represents a promising new approach to cancer therapy since its inhibition may lead to the selective killing of tumor cells over normal cells.

We have shown that PX-478 inhibits growth of hypoxic cells to a greater extent than under normoxic conditions. This is an important finding as hypoxia commonly causes resistance to both radiation and chemotherapy. Therefore we investigated the effect of PX-478 on the HIF pathway. PX-478 inhibited HIF-1α protein leading to decreased HIF-1 transactivation and expression of the downstream target gene VEGF. PX-478 also decreased HIF-1α in vivo at a non-toxic dose. Interestingly, this inhibition was shown to occur independently of the VHL pathway, the most well-studied mechanism for controlling HIF-1α stabilisation. This is an important finding as over 80% of renal cancers show inactivating mutations, or complete loss of the VHL gene. However, many other factors have been shown to affect HIF-1α protein including the P53 tumor suppressor pathway as well as oncogenes signaling through the PI3K and MAPK pathways.

Interestingly, several recent studies have also reported indirect inhibition of the HIF-1 pathway in a VHL independent manner. These include inhibition of PI3K using LY294002, inhibition of the molecular chaperone HSP90 using geldanaycin, and inhibition of redox signaling by PX-12 and pleurotin. Indeed, thioredoxin reductase activity was shown in this study to be significantly decreased at concentrations of PX-478 which correlate well with HIF-1α inhibition.

Thioredoxin reductase is a selenocysteine-containing flavoprotein that catalyzes the NADPH-dependent reduction of the redox protein thioredoxin (Trx-1). The activity of thioredoxin is therefore dependent on thioredoxin reductases. Over-expression of Trx-1 has been linked to aggressive tumor growth, inhibited apoptosis and, recently, increased angiogenesis via the HIF-1 pathway. Through its redox activity, Trx-1 regulates the activity of enzymes such as apoptosis signal regulating kinase-1 (ASK1) and protein kinases C α,δ,ε and ζ, and increases the DNA binding and transactivating activity of transcription factors including NF-κB, the glucocorticoid receptor and p53. Mouse WEHI7.2 lymphoma cells transfected with human Trx-1 form tumors in immunodeficient scid mice that grow more rapidly and show less spontaneous and drug induced apoptosis than vector-alone transfected cells. A redox inactive mutant Trx-1 acts as a dominant negative to inhibit human breast cancer MCF-7 and WEHI7.2 cell growth. Trx-1 expression is increased in many cancers. More recently, increased Trx-1 levels have been correlated with decreased apoptosis and patient survival in gastric cancer and decreased patient survival in non small-cell lung cancer.

However, the precise mechanism for how Trx-1 signaling affects the HIF-1 pathway remains unclear. Previous studies have suggested that Trx-1 affects HIF-1α protein stability as well as HIF-1 transactivation via the dual function DNA repair endonuclease and redox regulatory protein redox-factor-1 (Ref-1). Trx-1 can directly reduce Ref-1 and promotes the binding of the transcription coactivator complex Creb-binding protein (CBP)/p300 to the C-terminal transactivation domain of HIF-1α leading to increased HIF-1 transactivation. However, although inhibition of this process could account, at least in part, for the inhibition of HIF-1α transactivation observed in the present study it does not explain the decrease in HIF-1α protein levels seen upon inhibition of Trx-1.

A recent study has shown that Trx-1 binds to, and inhibits, the tumor-suppressor protein PTEN leading to activation of the PI3K pathway through AKT. In light of the findings that the PI3K/AKT pathway is involved in the stabilization and activation of HIF and that the PI3K inhibitor LY294002 also decreases HIF-1α protein in a VHL independent manner it is possible Trx-1 may affect HIF-1α through this pathway. Although recent studies suggest that this is cell-type dependent and, when observed, lies downstream of HIF activation or in a parallel pathway. We are currently investigating this possibility.

In summary we have shown that PX-478 is a novel anti-cancer agent which inhibits hypoxia-induced HIF-1α protein, HIF-1 transactivation and expression of the downstream target VEGF. Inhibition lasted up to 4 h after removal of the drug. PX-478 acts in a VHL independent manner, probably via inhibition of thioredoxin reductase. PX-478 also decreased HIF-1α protein in vivo. PX-478 therefore represents a promising anti-cancer agent which may lead to selective killing of cancer cells over normal cells.

Recently, several drugs have been reported to indirectly inhibit the HIF-1 complex. As mentioned above, the HSP90 inhibitor geldanamycin has been reported to inhibit HIF-1α protein by a pVHL-independent mechanism. A number of camptothecin analogues have also been identified as inhibitors of HIF-1α protein and transactivation using a high-throughput screening approach. Although it is not clear if these compounds simply inhibit general transcription via topoisomerase I inhibition rather being specific HIF-1 inhibitors. DX-2-1 (a carbomycin derivitive) was also identified using the same screen but is known to affect a number of transcription factors in addition to HIF-1. We have also identified two inhibitors of the thioredoxin-1 redox system, PX-12 and pleurotin, as inhibitors of HIF-1α protein, HIF-1 transactivation and hypoxia-induced VEGF production in vitro and HIF-1α protein in vivo.

Figure 10:
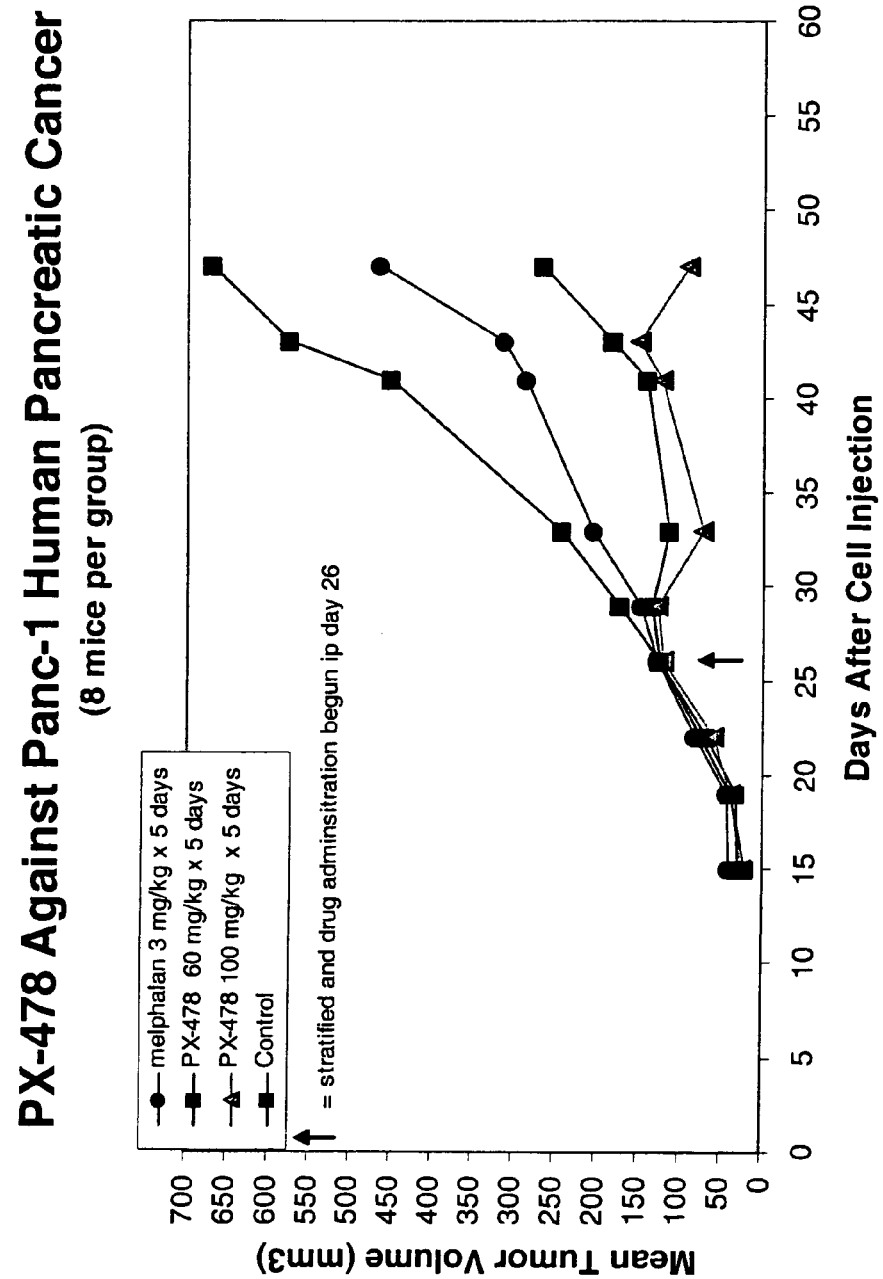
FIG. 10 illustrates the effect of PX-478 against Panc-1 human pancreatic cancer.
Figure 11:
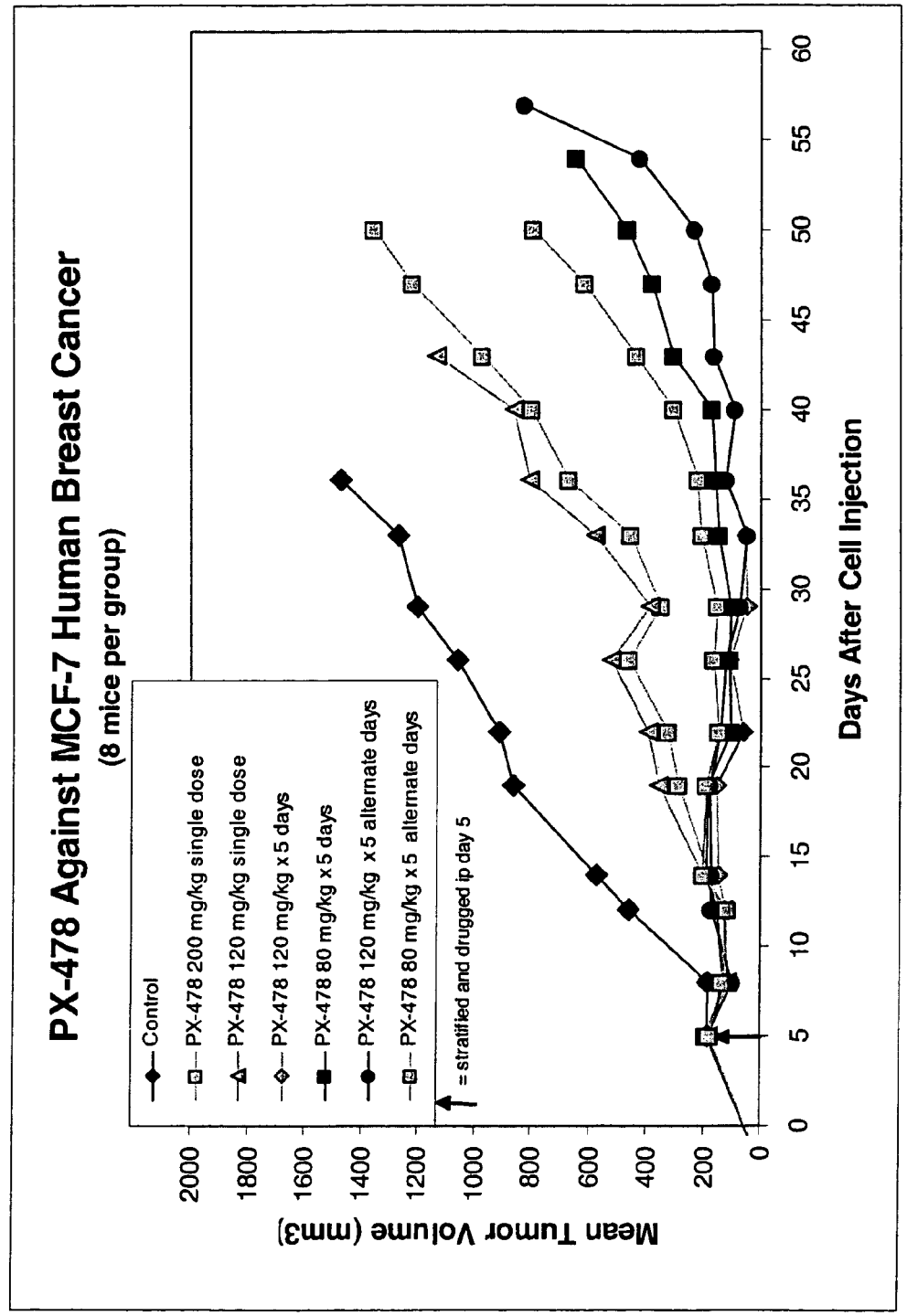
FIG. 11 illustrates the effect of PX-478 against MF-7 human breast cancer.
Figure 12:
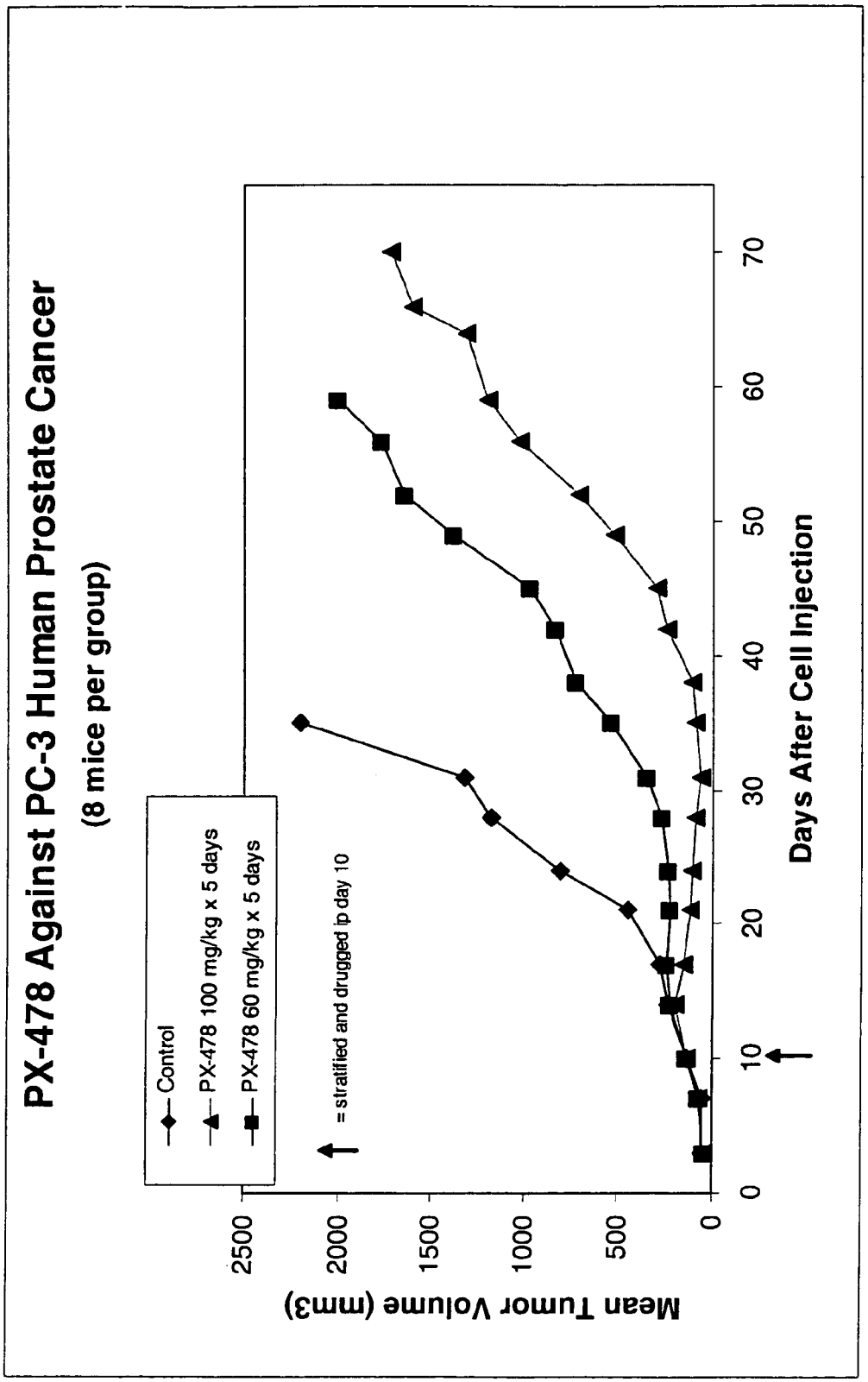
FIG. 12 illustrates the effect of PX-478 against PC-3 human prostate cancer (8 mice per group).
Figure 13:
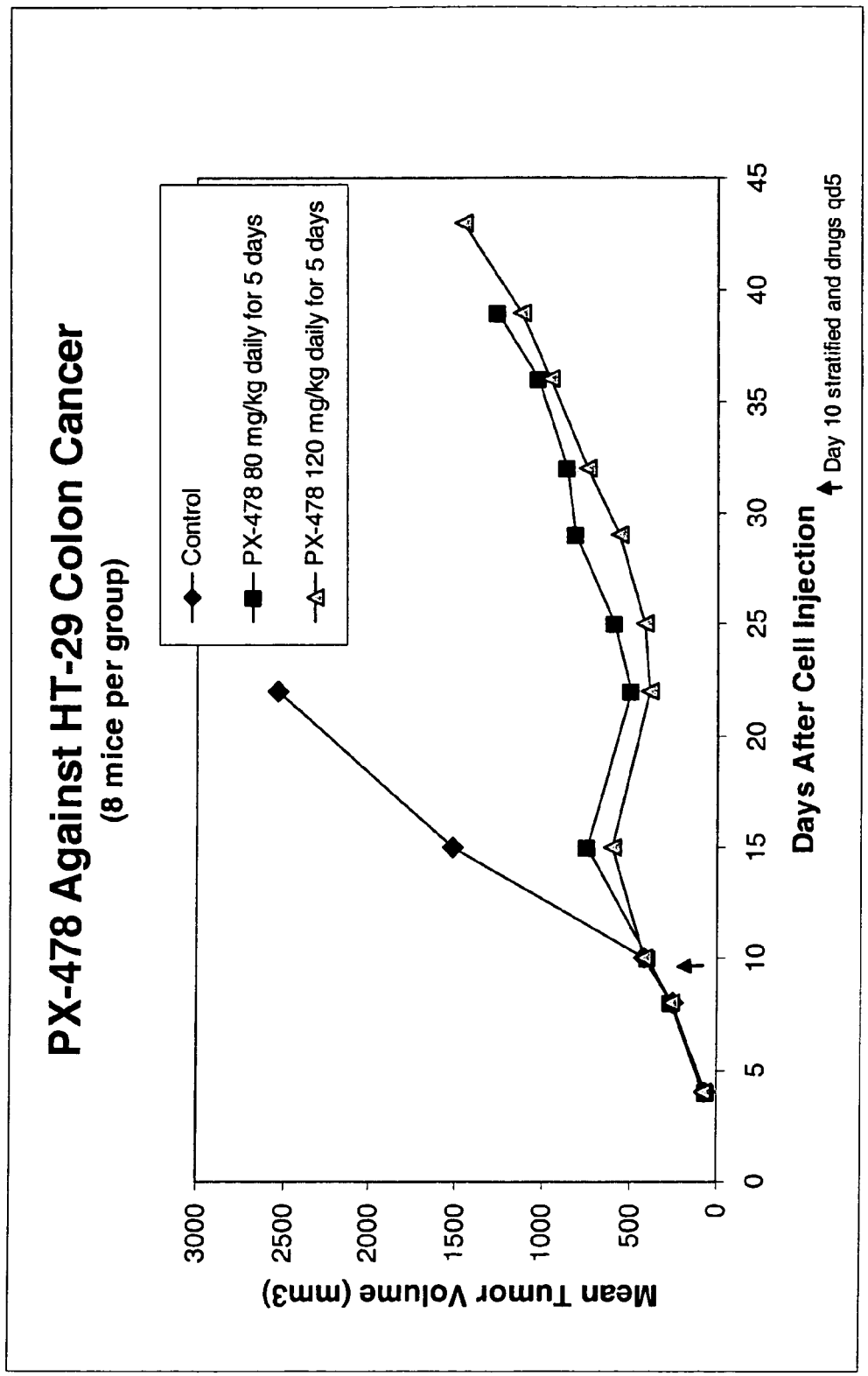
FIG. 13 illustrates the effect of PX-478 against HT-29 colon cancer (8 mice per group).

FIG. 10-13 illustrates the effect of PX-478 against Panc-1 human pancreatic cancer (FIG. 10); MCF-7 Human Breast Cancer (FIG. 11); Human Prostate Cancer (FIG. 12); and HT-29 Colon Cancer (FIG. 13).

Figure 14:
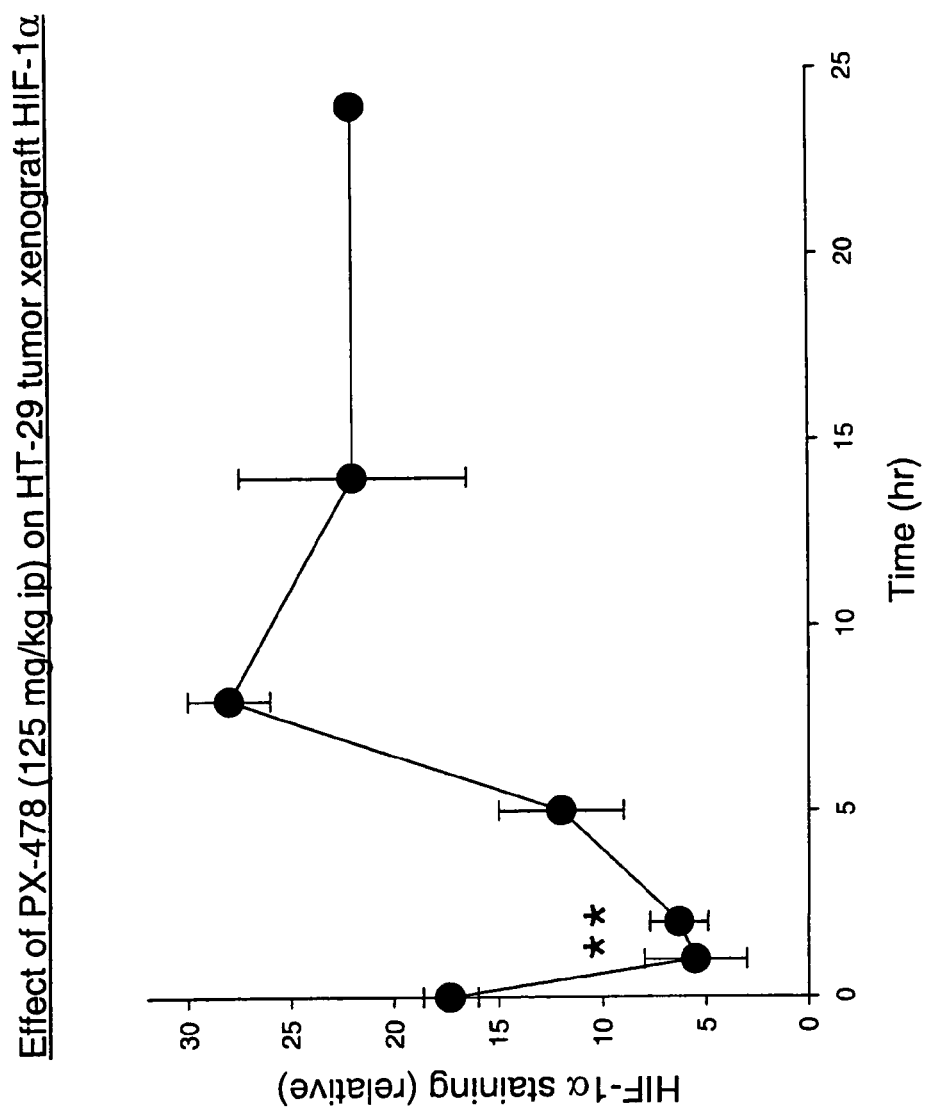
FIG. 14 illustrates the effect of PX-478 (125 mg/kg ip) on HT-29 tumor xenograft HIF-1α.

FIG. 14 illustrates the effect of PX-478 on HT-29 Tumor xenograph HIF-12.

FIG. 15 illustrates the effect of PX-478 on plasma VEGF levels.

The invention also relates to pharmaceutical formulations containing such compounds. The formulation may also comprise one or more of such compounds together with one or more of a pharmaceutically acceptable carrier, a diluent, an aqueous solution, an adjuvant, or another compound useful in treating a patient in need thereof. Suitable formulations may include buffered solutions containing one or more of the compounds administered as intravenous infusion. The invention includes a method of medical treatment comprising the use of such compounds. The method may also comprise using such compounds together with other methods of medical treatment useful in treating particular diseases, such as radiotherapy or chemotherapy.

While preferred embodiments have been described in detail, variations may be made to these embodiments without departing from the spirit or scope of the attached claims.

What is claimed is:

1. A method of inhibiting angiogenic growth in a patient in need thereof comprised of administering a compound having the formula:

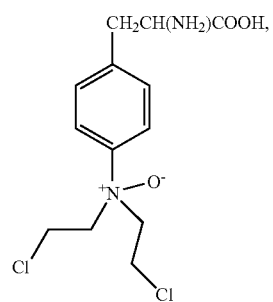

wherein the angiogenic growth is associated with a cancer selected from prostate cancer, breast cancer, colon cancer, pancreatic cancer, renal cancer and combinations thereof.

2. The method of claim 1, wherein the compound is administered together with a pharmaceutically acceptable carrier or diluent.

3. A method of inhibiting VEGF in a patient in need thereof comprised of administering a compound having the formula:

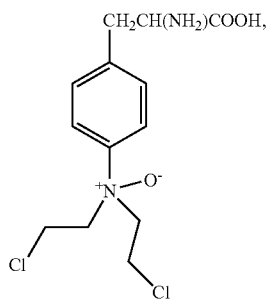

wherein the VEGF is associated with a cancer selected from prostate cancer, breast cancer, colon cancer, pancreatic cancer, renal cancer and combinations thereof.

4. The method of claim 3, wherein the compound is administered together with a pharmaceutically acceptable carrier or diluent.

5. A method of inhibiting tumor formation in a patient in need thereof comprised of administering a compound having the formula:

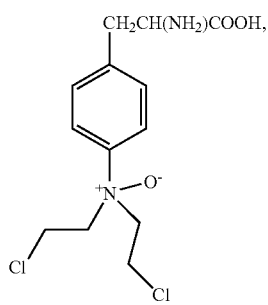

wherein the tumor formation is associated with a cancer selected from prostate cancer, breast cancer, colon cancer, pancreatic cancer, renal cancer and combinations thereof.

6. The method of claim 5, wherein the compound is administered together with a pharmaceutically acceptable carrier or diluent.

7. A method of treating breast cancer comprising administering a compound having the formula:

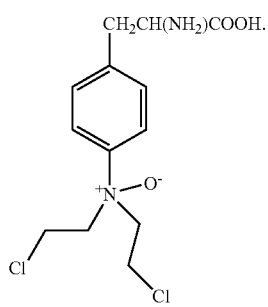

8. A method of treating prostate cancer comprising administering a compound having the formula:

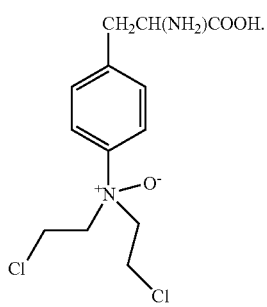

9. A method of treating pancreatic cancer comprising administering a compound having the formula:

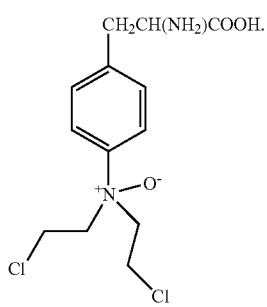

10. A method of treating colon cancer comprising administering a compound having the formula:

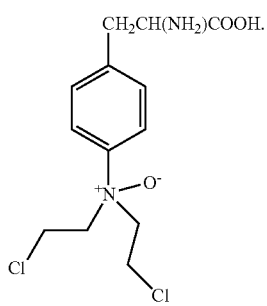

11. A method of treating renal cancer comprising administering a compound having the formula:

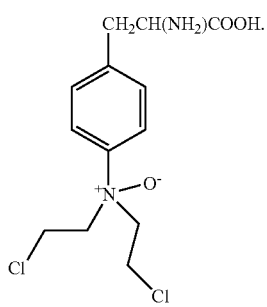

12. The method of claim 1 wherein the compound is administered in an amount effective to inhibit said angiogenic growth.

13. The method of claim 3 wherein the compound is administered in an amount effective to inhibit said VEGF.

14. The method of claim 5 wherein the compound is administered in an amount effective to inhibit said tumor formation.

15. The method of claim 7 wherein the compound is administered in an amount effective to treat said breast cancer.

16. The method of claim 8 wherein the compound is administered in an amount effective to treat said prostate cancer.

17. The method of claim 9 wherein the compound is administered in an amount effective to treat said pancreatic cancer.

18. The method of claim 10 wherein the compound is administered in an amount effective to treat said colon cancer.

19. The method of claim 11 wherein the compound is administered in an amount effective to treat said renal cancer.

* * * * *

UNITED STATES PATENT AND TRADEMARK OFFICE
CERTIFICATE OF CORRECTION

PATENT NO. : 7,399,785 B2  
APPLICATION NO. : 10/929,156  
DATED : July 15, 2008  
INVENTOR(S) : Lynn Kirkpatrick, Garth Powis and Sarah J. Welsh Page 1 of 1

It is certified that error appears in the above-identified patent and that said Letters Patent is hereby corrected as shown below:

Please add at column 1, line 19:

--This invention was made with government support under U19 CA052995, U54 CA090821 and RO1 CA098920 awarded by NIH. The government has certain rights in this invention.

Signed and Sealed this

Seventh Day of October, 2008

JON W. DUDAS  
*Director of the United States Patent and Trademark Office*

UNITED STATES PATENT AND TRADEMARK OFFICE
CERTIFICATE OF CORRECTION

PATENT NO. : 7,399,785 B2  Page 1 of 1
APPLICATION NO. : 10/929156
DATED : July 15, 2008
INVENTOR(S) : Lynn Kirkpatrick, Garth Powis and Sarah J. Welsh It is certified that error appears in the above-identified patent and that said Letters Patent is hereby corrected as shown below:

Title page item [73]
Assignee: Prolx Pharmaceuticals Corp., Tucson, AZ (US)

should read:

Assignee: Prolx Pharmaceuticals Corp., Tucson, AZ (US); Arizona Board of Regents, acting on behalf of The University of Arizona, Tucson, AZ (US)

Signed and Sealed this

Seventeenth Day of March, 2009

JOHN DOLL
*Acting Director of the United States Patent and Trademark Office*